United States Patent
Davis et al.

(10) Patent No.: US 10,314,340 B2
(45) Date of Patent: Jun. 11, 2019

(54) REFILLABLE AEROSOL DELIVERY DEVICE AND RELATED METHOD

(71) Applicant: RAI STRATEGIC HOLDINGS, INC., Winston-Salem, NC (US)

(72) Inventors: Michael F. Davis, Clemmons, NC (US); Percy D. Phillips, Pfafftown, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 5 days.

(21) Appl. No.: 15/493,919

(22) Filed: Apr. 21, 2017

(65) Prior Publication Data

US 2018/0303160 A1   Oct. 25, 2018

(51) Int. Cl.
*A24F 47/00* (2006.01)

(52) U.S. Cl.
CPC .................. *A24F 47/008* (2013.01)

(58) Field of Classification Search
CPC .................................................... A24F 47/008
See application file for complete search history.

(56) References Cited

U.S. PATENT DOCUMENTS

| | | |
|---|---|---|
| 1,514,682 A | 11/1924 | Wilson |
| 1,771,366 A | 7/1930 | Wyss et al. |
| 2,057,353 A | 10/1936 | Whittemore, Jr. |
| 2,104,266 A | 1/1938 | McCormick |
| 3,200,819 A | 8/1965 | Gilbert |
| 3,479,561 A | 11/1969 | Janning |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |

(Continued)

FOREIGN PATENT DOCUMENTS

| | | |
|---|---|---|
| AU | 276250 | 7/1965 |
| CA | 2 641 869 | 5/2010 |

(Continued)

*Primary Examiner* — James Harvey
(74) *Attorney, Agent, or Firm* — Womble Bond Dickinson (US) LLP

(57) ABSTRACT

The present disclosure is directed to an aerosol delivery device. The aerosol delivery device may include one or more fill ports. Thereby, a reservoir of the aerosol delivery device may be refillable. The fill ports may be defined in a base of a cartridge of the aerosol delivery device. The aerosol delivery device may further include a flow director. An atomizer may extend through the flow director transversely to a longitudinal length of the flow director. The atomizer may include a liquid transport element with a capillary channel extending therethrough, which may receive aerosol precursor composition from the reservoir. There aerosol precursor composition may be drawn through the liquid transport element to a heating element of the atomizer, which may vaporize the aerosol precursor composition.

20 Claims, 9 Drawing Sheets

(56) References Cited

U.S. PATENT DOCUMENTS

| | | | |
|---|---|---|---|
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 9,795,169 B1 * | 10/2017 | Zhu .................. A24F 47/008 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0238396 A1 | 8/2014 | Buchberger |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0283825 A1 | 9/2014 | Buchberger |
| 2014/0299125 A1 | 10/2014 | Buchberger |
| 2014/0345631 A1 | 11/2014 | Bowen et al. |
| 2014/0360514 A1 | 12/2014 | Zhu |
| 2014/0360516 A1 | 12/2014 | Liu |
| 2015/0007838 A1 | 1/2015 | Fernando et al. |
| 2015/0053217 A1 | 2/2015 | Steingraber et al. |
| 2015/0335070 A1 * | 11/2015 | Sears .................. H05B 1/0288 131/328 |

(56) References Cited

U.S. PATENT DOCUMENTS

| | | | |
|---|---|---|---|
| 2015/0335071 A1* | 11/2015 | Brinkley | F22B 1/284 |
| | | | 131/328 |
| 2016/0037826 A1 | 2/2016 | Hearn et al. | |
| 2016/0073692 A1 | 3/2016 | Alarcon et al. | |
| 2017/0013880 A1 | 1/2017 | O'Brien et al. | |
| 2017/0020190 A1* | 1/2017 | Chang | A24F 47/008 |
| 2017/0020193 A1* | 1/2017 | Davis | A24F 47/008 |
| 2017/0036848 A1* | 2/2017 | Chury | B29C 65/08 |
| 2017/0311644 A1* | 11/2017 | Collett | A24F 47/008 |
| 2018/0027876 A1* | 2/2018 | Watson | A24B 15/283 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 206 079 029 | 4/2017 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 3 153 199 | 4/2017 |
| GB | 2469850 | 11/2010 |
| GB | 2 531 830 | 5/2016 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2014/195859 | 12/2014 |

* cited by examiner

-- PRIOR ART --

-- PRIOR ART --

| 502 | RETAIN AN AEROSOL PRECURSOR COMPOSITION IN A RESERVOIR DEFINED BETWEEN A FLOW DIRECTOR AND AN OUTER BODY, THE FLOW DIRECTOR EXTENDING BETWEEN A FIRST FLOW DIRECTOR END AND A SECOND FLOW DIRECTOR END |

| 504 | DIRECT THE AEROSOL PRECURSOR COMPOSITION FROM THE RESERVOIR THROUGH A LIQUID TRANSPORT ELEMENT OF AN ATOMIZER EXTENDING THROUGH THE FLOW DIRECTOR AT A POSITION BETWEEN THE FIRST FLOW DIRECTOR END AND THE SECOND FLOW DIRECTOR END |

| 506 | RECEIVE AN ELECTRICAL CURRENT THROUGH A HEATING ELEMENT OF THE ATOMIZER |

| 508 | VAPORIZE AT LEAST A PORTION OF THE AEROSOL PRECURSOR COMPOSITION TO PRODUCE AN AEROSOL WITHIN THE FLOW DIRECTOR |

FIG. 9

REFILLABLE AEROSOL DELIVERY DEVICE AND RELATED METHOD

BACKGROUND

Field of the Disclosure

The present disclosure relates to aerosol delivery devices such as electronic cigarettes, and more particularly to aerosol delivery devices including an atomizer. The atomizer may be configured to heat an aerosol precursor composition, which may be made or derived from tobacco or otherwise incorporate tobacco, to form an inhalable substance for human consumption.

Description of Related Art

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

However, it may be desirable to provide aerosol delivery devices with alternate configurations. Such configurations may provide for refilling and reuse of the aerosol delivery device. Thus, advances with respect to aerosol delivery devices may be desirable.

BRIEF SUMMARY OF THE DISCLOSURE

The present disclosure relates to aerosol delivery devices configured to produce aerosol and which aerosol delivery devices, in some embodiments, may be referred to as electronic cigarettes. In one aspect, an aerosol delivery device is provided. The aerosol delivery device may include an outer body, a base, and a flow director extending from a first flow director end to a second flow director end through the outer body such that a reservoir may be defined between the flow director and the outer body. The reservoir may define an open space configured to receive an aerosol precursor composition. Additionally, the aerosol delivery device may include an atomizer extending through the flow director at a position between the first flow director end and the second flow director end. The atomizer may include a liquid transport element and a heating element configured to vaporize at least a portion of the aerosol precursor composition to produce an aerosol within the flow director.

In some embodiments the liquid transport element may include a capillary channel extending therethrough. The liquid transport element may include a porous monolith. The heating element may include a wire defining a plurality of coils extending around the liquid transport element. The aerosol delivery device may additionally include first and second connectors contacting the coils at first and second opposing ends of the heating element.

In some embodiments a longitudinal axis of the liquid transport element may extend substantially perpendicularly to a longitudinal axis of the flow director. The outer body may be sealed to the base. The outer body may engage the base via threaded engagement. The aerosol delivery device may additionally include an O-ring compressed between the outer body and the base. The aerosol delivery device may further include a mouthpiece. The mouthpiece may be sealed to the outer body and the flow director. The base may include one or more fill ports configured to receive the aerosol precursor composition therethrough. The atomizer may be sealed to the flow director.

In an additional aspect, an aerosol delivery device operation method is provided. The method may include retaining an aerosol precursor composition in a reservoir defined between a flow director and an outer body. The flow director may extend between a first flow director end and a second flow director end. Further, the method may include directing the aerosol precursor composition from the reservoir through a liquid transport element of an atomizer extending through the flow director at a position between the first flow director end and the second flow director end. The method may additionally include receiving an electrical current through a heating element of the atomizer. The method may further include vaporizing at least a portion of the aerosol precursor composition to produce an aerosol within the flow director.

In some embodiments, the method may further include receiving the aerosol precursor composition through one or more fill ports defined in a base. Directing the aerosol precursor composition through the liquid transport element may include directing the aerosol precursor composition through a capillary channel. Directing the aerosol precursor composition through the liquid transport element may further include directing the aerosol precursor composition through a porous monolith to the heating element.

In some embodiments receiving the electrical current through the heating element may include receiving the electrical current through a wire defining a plurality of coils extending around the liquid transport element. Additionally, the method may include directing the aerosol out of the flow director through a mouthpiece. The method may further include retaining the aerosol precursor composition in the reservoir with a seal between the outer body and the base. The method may additionally include retaining the aerosol precursor composition in the reservoir with a seal between the mouthpiece and the outer body and a seal between the mouthpiece and the flow director.

These and other features, aspects, and advantages of the disclosure will be apparent from a reading of the following detailed description together with the accompanying drawings, which are briefly described below.

BRIEF DESCRIPTION OF THE FIGURES

Figure 1:
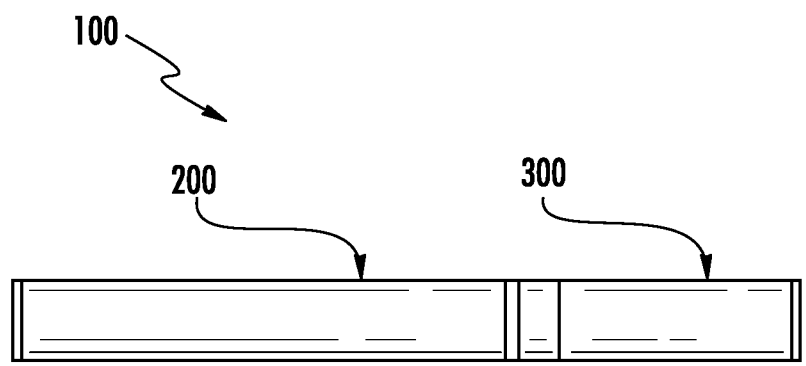
Figure 2:
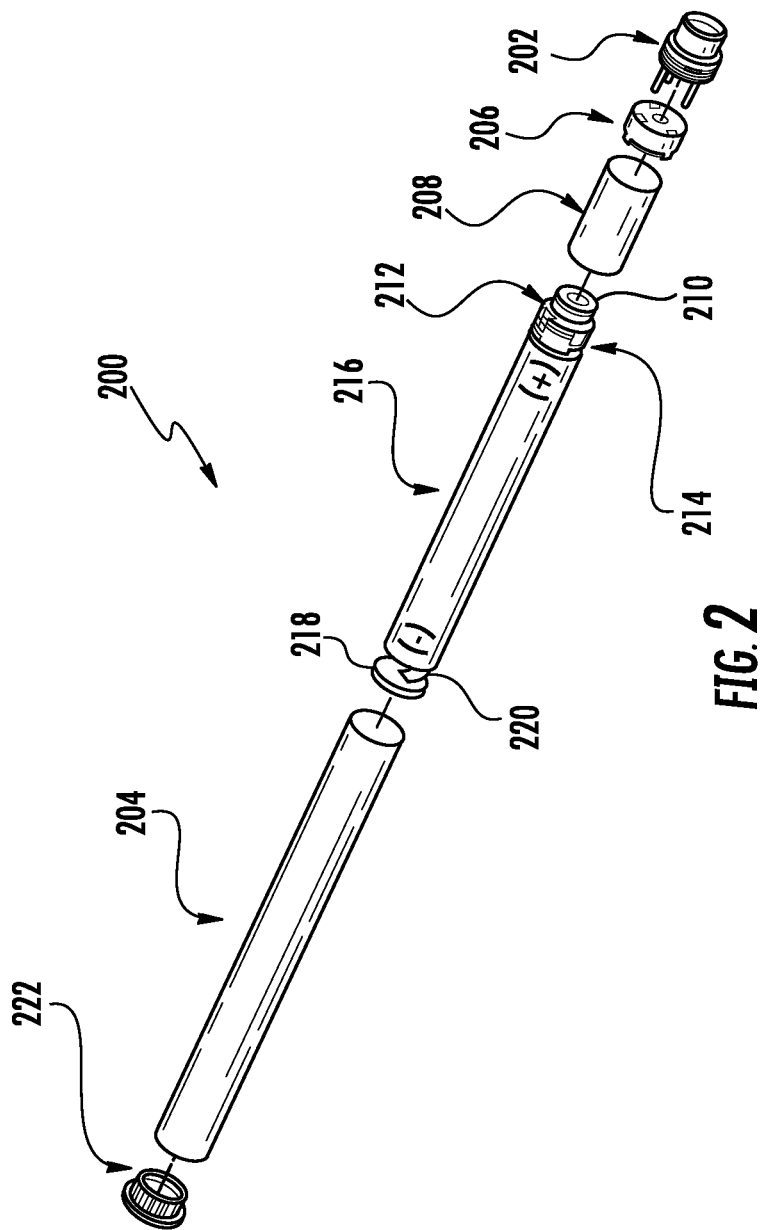
Figure 3:
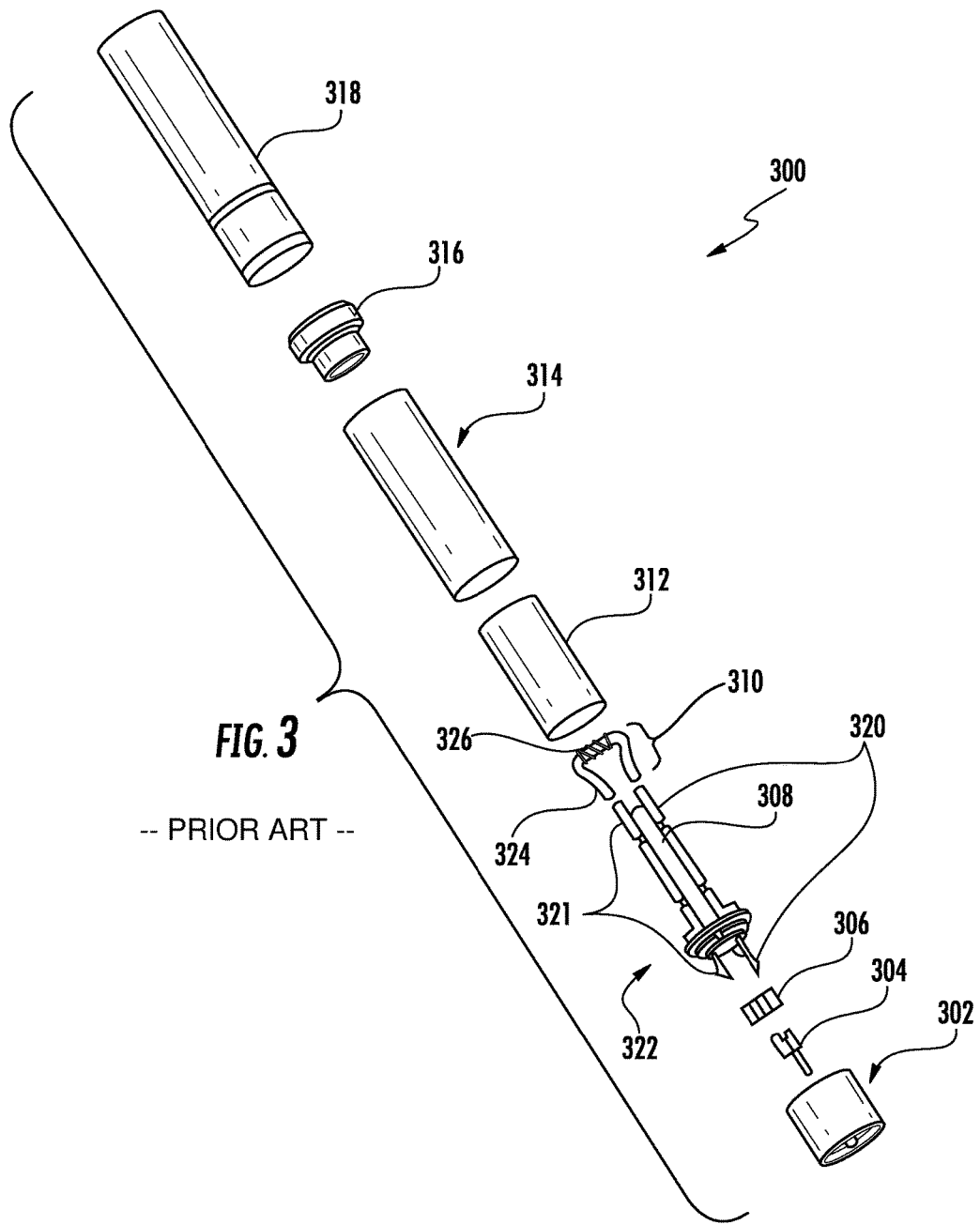
Figure 4:
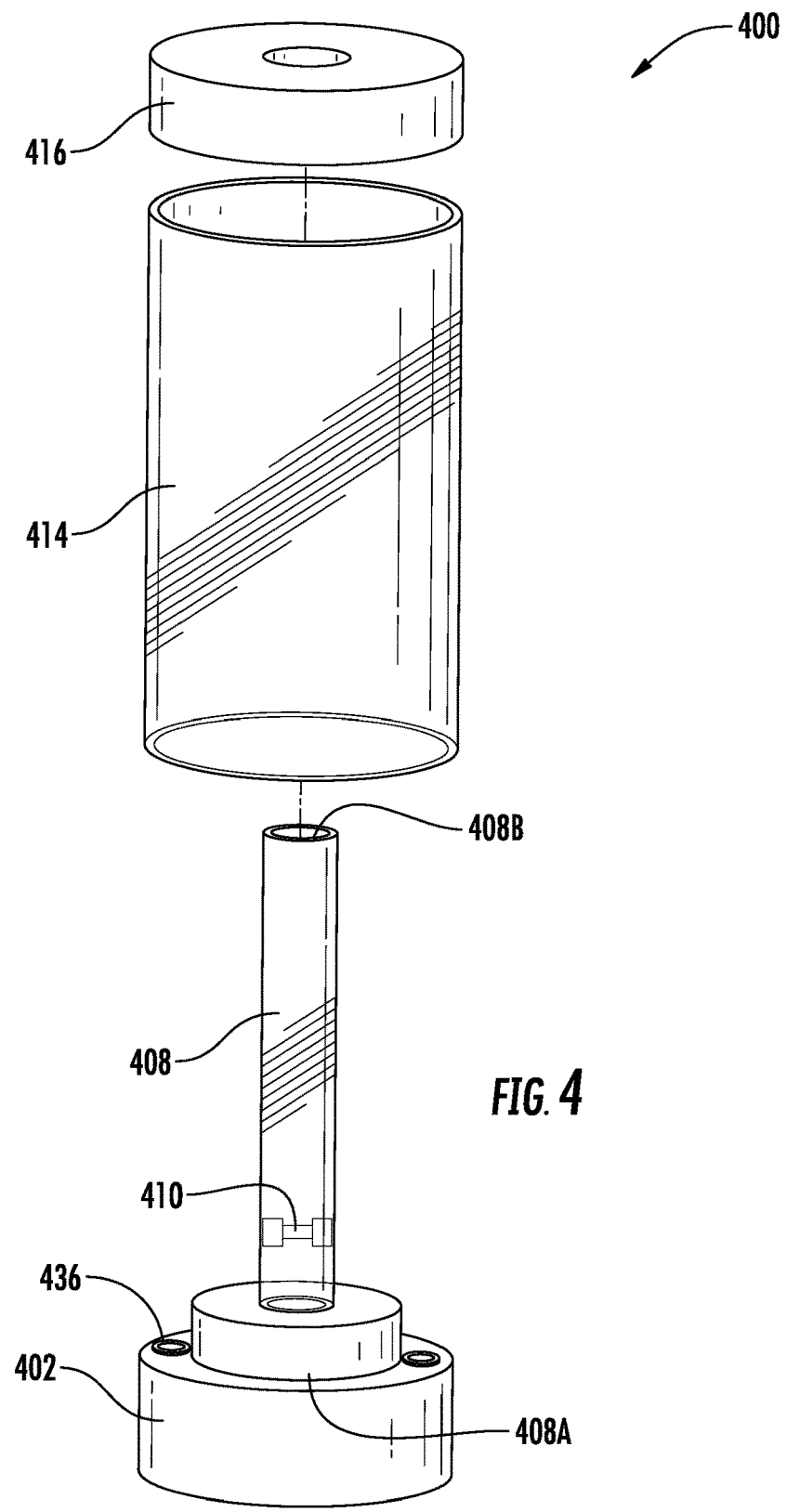
Figure 5:
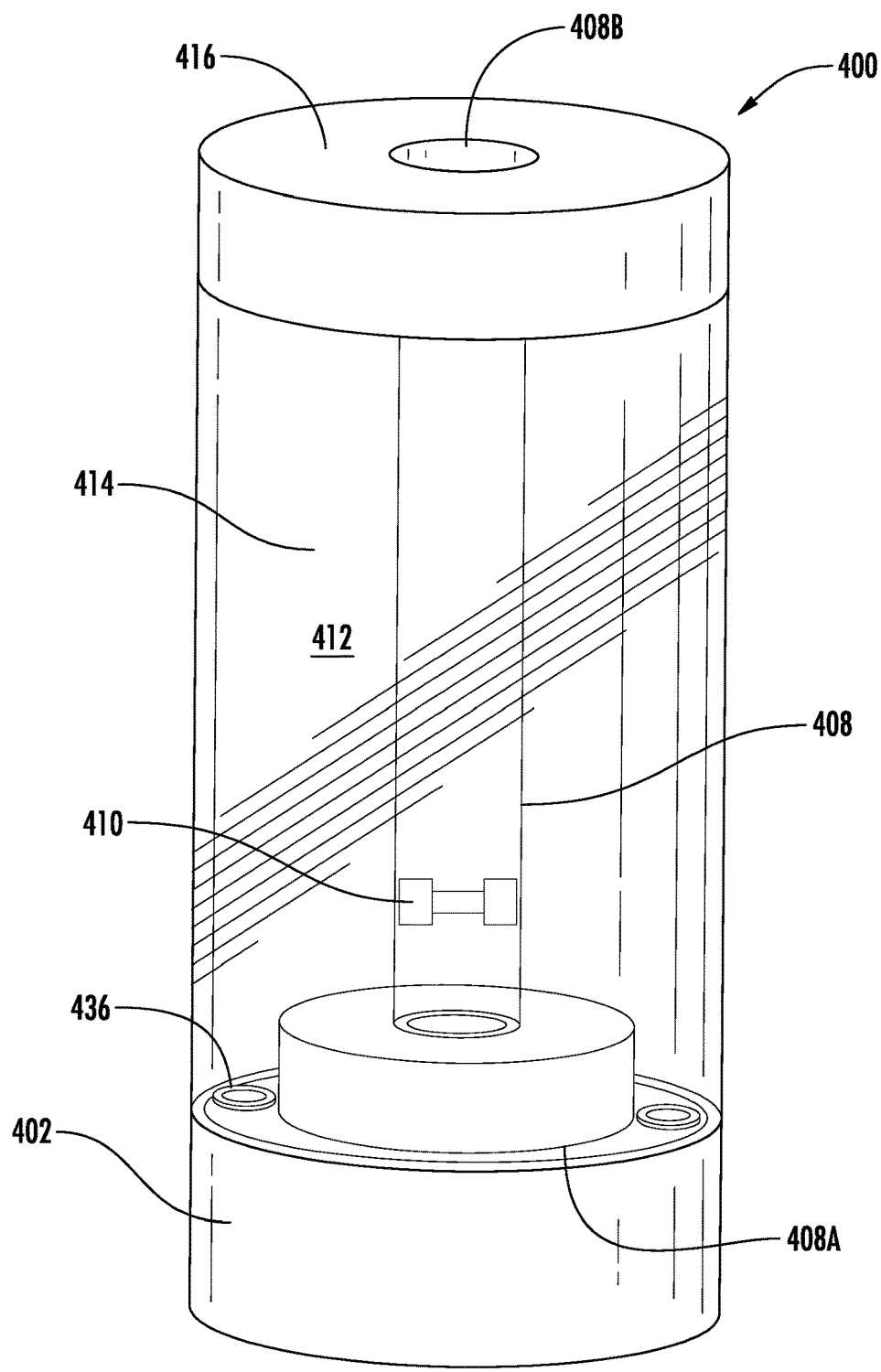
Figure 6:
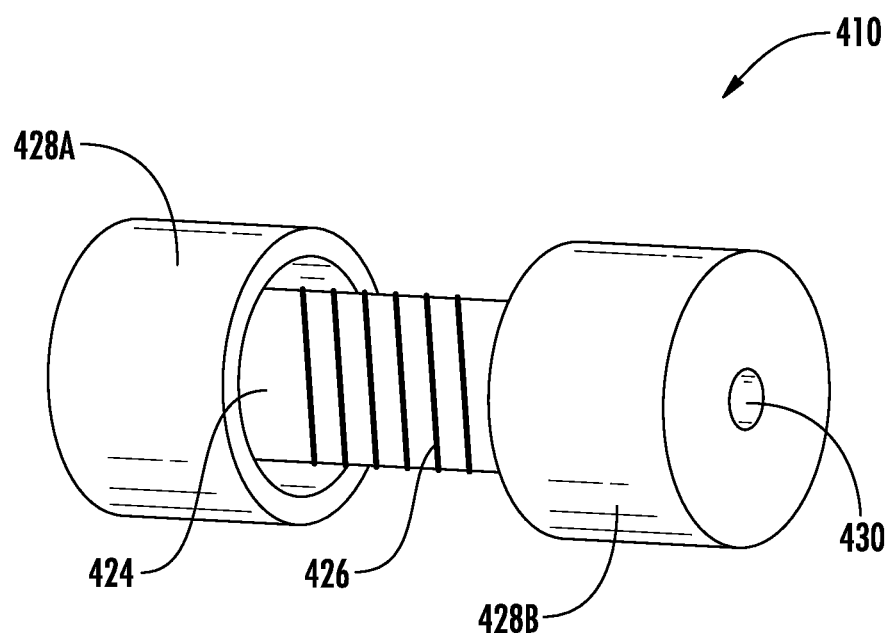

Having thus described the disclosure in the foregoing general terms, reference will now be made to the accompanying drawings, which are not necessarily drawn to scale, and wherein:

FIG. 1 illustrates a side view of an aerosol delivery device comprising a cartridge and a control body in an assembled configuration according to an example embodiment of the present disclosure;

FIG. 2 illustrates the control body of FIG. 1 in an exploded configuration according to an example embodiment of the present disclosure;

FIG. 3 illustrates the cartridge of FIG. 1 in an exploded configuration according to an example embodiment of the present disclosure;

FIG. 4 illustrates a partially-exploded view of a refillable cartridge according to an example embodiment of the present disclosure;

FIG. 5 illustrates the refillable cartridge of FIG. 4 in an assembled configuration;

FIG. 6 illustrates an enlarged perspective view of an atomizer of the refillable cartridge of FIG. 4;

Figure 7:
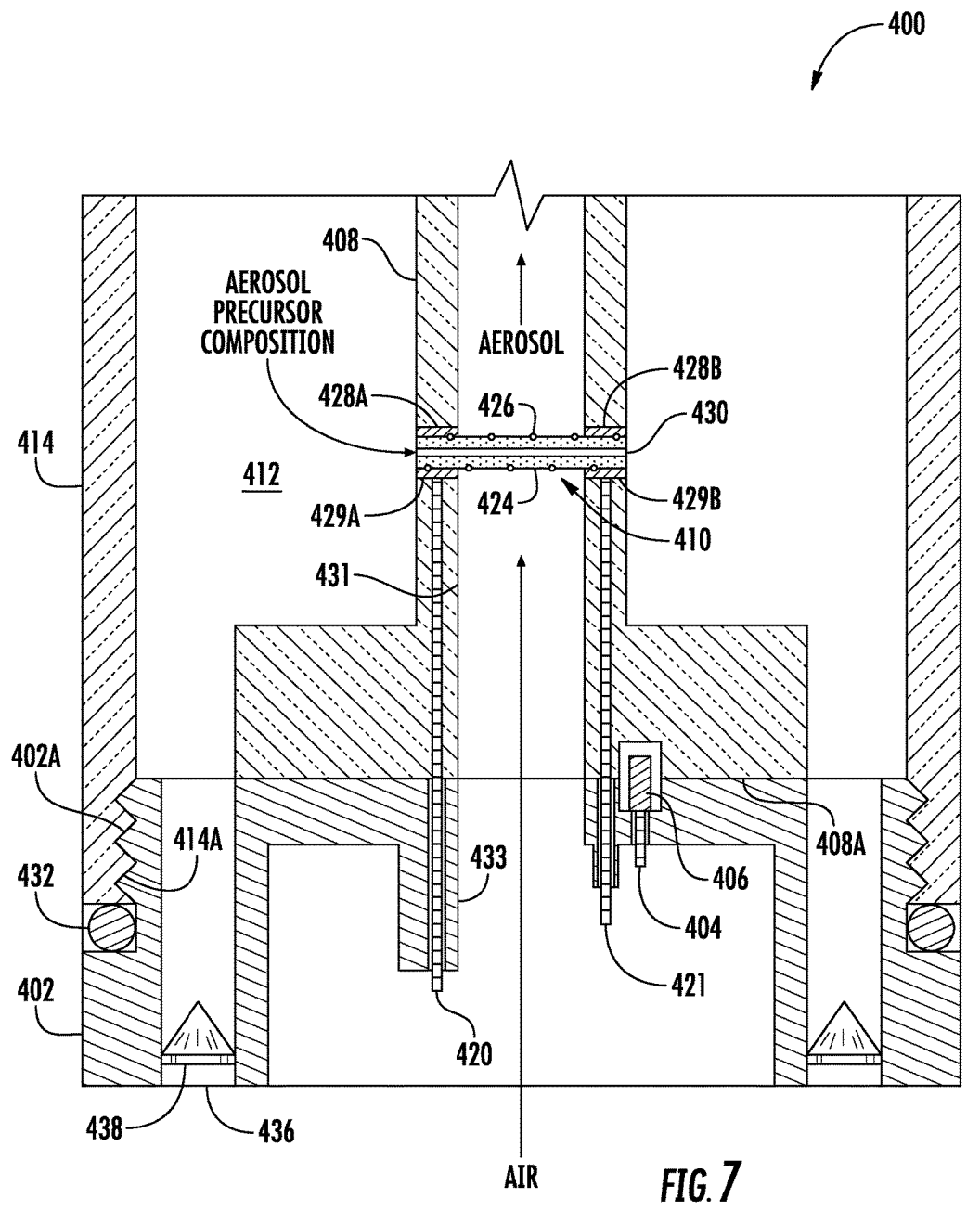

FIG. 7 illustrates a partial longitudinal sectional view through a lower portion of the cartridge of FIG. 4;

Figure 8:
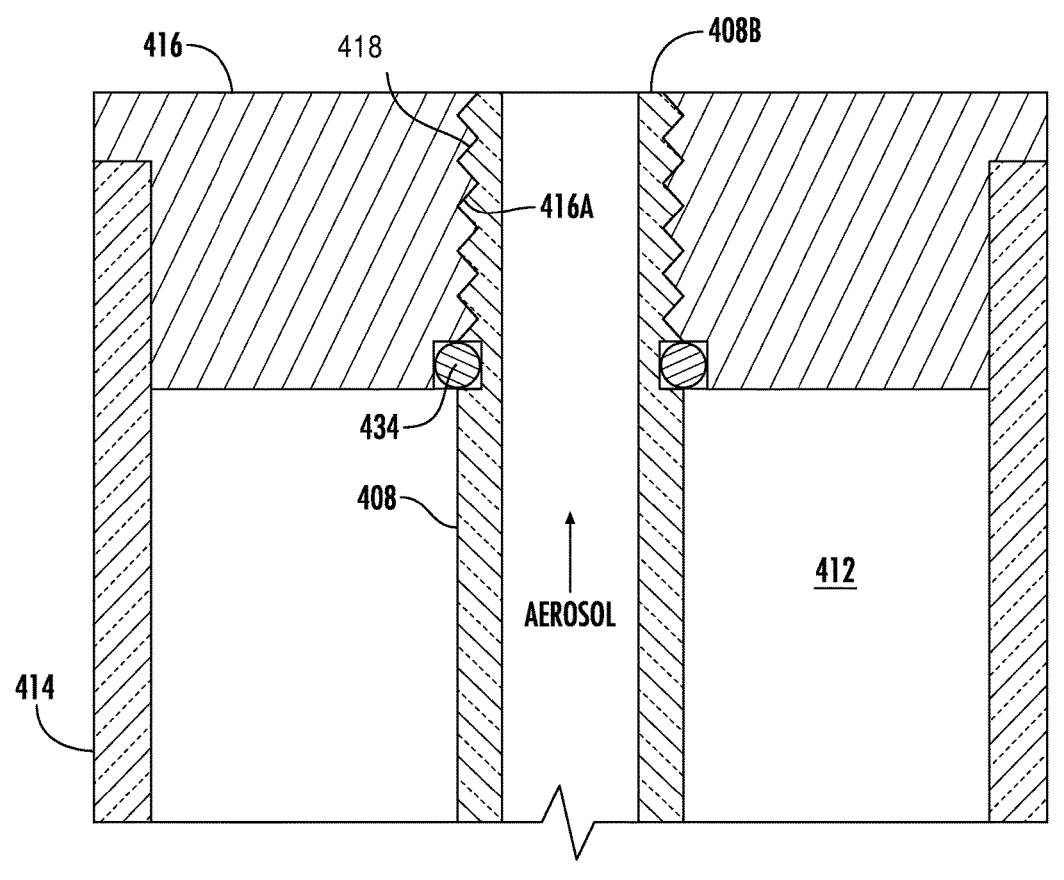

FIG. 8 illustrates a partial longitudinal sectional view through an upper portion of the cartridge of FIG. 4; and FIG. 9 schematically illustrates an aerosol delivery device operation method according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette or "e-cigarette."

While the systems are generally described herein in terms of embodiments associated with aerosol delivery devices such as so-called "e-cigarettes," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, a vapor is formed with subsequently condenses to an aerosol suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery and/or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

One example embodiment of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various mechanisms may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 300 and the control body 200 are in an assembled configuration. However, as noted above, various other configurations such as rectangular or fob-shaped may be employed in other embodiments. Further, although the aerosol delivery devices are generally described herein as resembling the size and shape of a traditional smoking article, in other embodiments differing configurations and larger capacity reservoirs, which may be referred to as "tanks," may be employed.

In specific embodiments, one or both of the cartridge 300 and the control body 200 may be referred to as being disposable or as being reusable. For example, the control body 200 may have a replaceable battery or a rechargeable battery and/or capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. No. 8,910,639 to Chang et al., which is incorporated herein by reference in its entirety.

FIG. 2 illustrates an exploded view of the control body 200 of the aerosol delivery device 100 (see, FIG. 1) according to an example embodiment of the present disclosure. As illustrated, the control body 200 may comprise a coupler 202, an outer body 204, a sealing member 206, an adhesive member 208 (e.g., KAPTON® tape), a flow sensor 210 (e.g., a puff sensor or pressure switch), a control component 212, a spacer 214, an electrical power source 216 (e.g., a capacitor and/or a battery, which may be rechargeable), a circuit board with an indicator 218 (e.g., a light emitting diode (LED)), a connector circuit 220, and an end cap 222. Examples of electrical power sources are described in U.S. Pat. No. 9,484,155 to Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In one embodiment the indicator 218 may comprise one or more light emitting diodes. The indicator 218 can be in communication with the control component 212 through the connector circuit 220 and be illuminated, for example, during a user draw on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other embodiments the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,528,569 to Newton; U.S. Pat. No. 8,707,965 to Newton; U.S. Pat. No. 8,794,231 to Thorens et al.; U.S. Pat. No. 8,851,083 to Oglesby et al.; U.S. Pat. Nos. 8,915, 254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

FIG. 3 illustrates the cartridge 300 of the aerosol delivery device 100 (see, FIG. 1) in an exploded configuration. As illustrated, the cartridge 300 may comprise a base 302, a control component terminal 304, an electronic component 306, a flow director 308, an atomizer 310, a reservoir 312 (e.g., a reservoir substrate), an outer body 314, a mouthpiece 316, a label 318, and first and second heating terminals 320, 321 according to an example embodiment of the present disclosure.

In some embodiments the first and second heating terminals 320, 321 may be embedded in, or otherwise coupled to, the flow director 308. For example, the first and second heating terminals 320, 321 may be insert molded in the flow director 308. Accordingly, the flow director 308 and the first and second heating terminals are collectively referred to herein as a flow director assembly 322. Additional description with respect to the first and second heating terminals 320, 321 and the flow director 308 is provided in U.S. Pat. Pub. No. 2015/0335071 to Brinkley et al., which is incorporated herein by reference in its entirety.

The atomizer 310 may comprise a liquid transport element 324 and a heating element 326. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to Depiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the control component terminal 304, the electronic component 306, the flow director 308, the atomizer 310, and the reservoir 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some embodiments the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

The reservoir 312 may be configured to hold an aerosol precursor composition. Representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Embodiments of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein. Additional description with respect to embodiments of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties.

The reservoir 312 may comprise a plurality of layers of nonwoven fibers formed into the shape of a tube encircling the interior of the outer body 314 of the cartridge 300. Thus, liquid components, for example, can be sorptively retained by the reservoir 312. The reservoir 312 is in fluid connection with the liquid transport element 324. Thus, the liquid transport element 324 may be configured to transport liquid from the reservoir 312 to the heating element 326 via capillary action or other liquid transport mechanism.

As illustrated, the liquid transport element 324 may be in direct contact with the heating element 326. As further illustrated in FIG. 3, the heating element 326 may comprise a wire defining a plurality of coils wound about the liquid transport element 324. In some embodiments the heating element 326 may be formed by winding the wire about the liquid transport element 324 as described in U.S. Pat. No. 9,210,738 to Ward et al., which is incorporated herein by reference in its entirety. Further, in some embodiments the wire may define a variable coil spacing, as described in U.S. Pat. No. 9,277,770 to DePiano et al., which is incorporated herein by reference in its entirety. Various embodiments of materials configured to produce heat when electrical current is applied therethrough may be employed to form the heating element 326. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic).

However, various other embodiments of methods may be employed to form the heating element 326, and various other embodiments of heating elements may be employed in the atomizer 310. For example, a stamped heating element may be employed in the atomizer, as described in U.S. Pat. No. 9,491,974 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320 and the second heating terminal 321 (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic component 306 may form an electrical connection with the control body through the control component terminal 304. The control body 200 may thus employ the electronic component 212 (see, FIG. 2) to determine whether the cartridge 300 is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on the mouthpiece 316 of the cartridge 300 of the aerosol delivery device 100 (see, FIG. 1). This may pull air through an opening in the control body 200 (see, e.g., FIG. 2) or in the cartridge 300. For example, in one embodiment an opening may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other embodiments. As noted above, in some embodiments the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200; see, FIG. 2) may sense the puff. When the puff is sensed, the control body 200 may direct current to the heating element 326 through a circuit including the first heating terminal 320 and the second heating terminal 321. Accordingly, the heating element 326 may vaporize the aerosol precursor composition directed to an aerosolization zone from the reservoir 312 by the liquid transport element 324. Thus, the mouthpiece 326 may allow passage of air and entrained vapor (i.e., the components of the aerosol precursor composition in an inhalable form) from the cartridge 300 to a consumer drawing thereon.

Various other details with respect to the components that may be included in the cartridge 300 are provided, for example, in U.S. Pat. App. Pub. No. 2014/0261495 to DePiano et al., which is incorporated herein by reference in its entirety. Additional components that may be included in the cartridge 300 and details relating thereto are provided, for example, in U.S. Pat. Pub. No. 2015/0335071 to Brinkley et al., which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another embodiment substantially the entirety of the cartridge may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the power source and control component. An example embodiment of a carbon-based cartridge is provided in U.S. Pat. App. Pub. No. 2013/0255702 to Griffith et al., which is incorporated herein by reference in its entirety.

However, in some embodiments it may be desirable to provide aerosol delivery devices with alternative configurations. In this regard, FIGS. 4 and 5 illustrate a cartridge 400 according to an additional example embodiment of the present disclosure. FIG. 4 illustrates the cartridge in an exploded configuration. FIG. 5 illustrates the cartridge 400 in an assembled configuration. Where not otherwise described and/or illustrated, the components of the cartridge 400 may be substantially similar to, or the same as, corresponding components described above in relation to FIG. 1 through FIG. 3.

As illustrated, the cartridge 400 may include a base 402, a flow director 408, an atomizer 410, an outer body 414, and a mouthpiece 416. A first end of the outer body 414 may engage the base 402. An opposing second end of the outer body 414 may engage the mouthpiece 416.

The flow director 408 may extend from a first end 408A at the base 402 through the outer body 414 to a second end 408B at the mouthpiece 416. Thereby, as illustrated in FIG. 5, a reservoir 412 may be defined between the flow director 408 and the outer body 414. The reservoir 412 may define an open space configured to receive an aerosol precursor composition. In one or more embodiments, a fibrous substrate may be present in at least a portion of the reservoir 412 to hold aerosol precursor composition similar to the reservoir substrate 312 illustrated in FIG. 3.

The atomizer 410 may be configured to vaporize the aerosol precursor composition received from the reservoir 412. In this regard, as illustrated in FIG. 6, the atomizer 410 may include a liquid transport element 424 and a heating element 426. The heating element 426 may comprise a wire defining a plurality of coils extending around the liquid transport element 424. Further, the atomizer 410 may include first and second connectors 428A, 428B contacting the coils at first and second opposing ends of the heating element 426. The connectors 428A, 428B may be configured to engage first and second heating terminals 420, 421 (see, FIG. 7) in order to supply power thereto.

The atomizer 410 may extend through the flow director 408. More particularly, a longitudinal axis of the liquid transport element 424 may extend substantially perpendicularly to a longitudinal axis of the flow director 408 such that the atomizer 410 extends across the flow director 408. In this regard, as illustrated in FIG. 7, the flow director 408 may include one or more apertures 429A, 429B extending therethrough, transverse to a longitudinal aperture 431 extending through the flow director. The atomizer 410 may extend at least partially through each of the apertures 429A, 429B such that the atomizer extends across the longitudinal aperture 431.

The liquid transport element 424 may include a capillary channel 430 extending therethrough. The capillary channel 430 may be configured to receive aerosol precursor composition from the reservoir 412. In this regard, as illustrated in FIG. 7, the capillary channel 430 may be in fluid communication with the reservoir 412. Accordingly, the aerosol precursor composition contained in the reservoir 412 may enter the liquid transport element 424 via the capillary channel 430. Further, the liquid transport element 424 may comprise a porous monolith. For example, the liquid transport element 424 may comprise a porous ceramic material composed of silica and/or alumina as exemplary materials. In some examples, where the liquid transport element 424 comprises a mixture of silica and alumina then a heater may be utilized. In some instances, the heater may be in the form of a conductive mesh, rather than a heater coil, formed from a plurality of crossing, conductive filaments that wrap around the liquid transport element 424 in order to provide a more uniform heat distribution. Example embodiments of conductive meshes are described in U.S. patent application Ser. No. 15/472,839 to Davis et al., filed Mar. 29, 2017, which is incorporated herein by reference in its entirety.

Alternatively, the porous liquid transport element may also be comprised of an electrically conducted ceramic (e.g., boron-doped silicon) that may act as a semiconductor for which resistance is controllable. As such, the liquid transport element may act as the heating element, thereby forgoing the necessity of a heating coil with a plurality of coils and desirably extending a lifetime of the atomizer. Accordingly, the aerosol precursor composition may be wicked from the capillary channel 430 generally radially outwardly such that the liquid transport element 424 is saturated and such that the aerosol precursor composition reaches the heating element 426.

The cartridge 400 may be coupled to a control body such as the control body 200 of FIG. 2. The control body 200 may verify that the cartridge 400 is genuine and/or perform other functions (e.g., preventing further heating of the heating element 426 after a predetermined number of cumulative seconds of heating have occurred, which may correspond to a substantially empty cartridge) by communicating with an electronic component 406 via an electronic component terminal 404. Thereafter, when the flow sensor 210 (see, FIG. 2) of the control body 200 detects a puff on the cartridge 400, the control body 200 may direct current from the electrical power source 216 (see, FIG. 2) to the cartridge. The electrical current may thereby be directed through the first and second heating terminals 420, 421 to the first and second connectors 428A, 428B.

In some embodiments, as illustrated, the first and second heating terminals 420, 421 may extend at least partially through the flow director 408. For example, the first and second heating terminals 420, 421 may be molded into the flow director 408 (e.g., in-molded in the flow director during the formation thereof) and extend along at least a portion of the length thereof. By way of further example, the first and second heating terminals 420, 421 may extend along a portion of a length thereof and terminate at a location at which the atomizer 410 extends across the flow director 408.

Thereby, the first and second heating terminals 420, 421 may contact the first and second connectors 428A, 428B, respectively, without blocking the apertures 429A, 429B in the flow director 408 through which the atomizer 410 extends. The other ends of the first and second heating terminals 420, 421 and the outer end of the electronic component terminal 404 may extend through openings defined in the base 402 such that the ends are exposed and configured for engagement with corresponding electrical contacts of a control body.

Accordingly, the electrical current may be directed through the heating element 426, in order to produce heat (e.g., via joule heating), or may be conducted directly through the liquid transport element. The heat may be transferred to the aerosol precursor composition directed through the liquid transport element 424 such that a vapor is produced inside of the flow director 408. The vapor may join with air directed through the flow director 408 and travel to a user via the mouthpiece 416 (see, e.g., FIG. 8). More particular, the vapor may be produced by the atomizer 410 within the longitudinal aperture 431 extending through the flow director 408. Thereby, by configuring the atomizer 410 such that it extends through the flow director 408, provision of a separate atomization cavity may not be necessary. In other words, by producing the vapor within the flow director 408, it may not be necessary to include a separate atomization cavity upstream or downstream of the flow director. Accordingly, the capacity of the reservoir 412 for a given cartridge size may be relatively larger.

In some embodiments the longitudinal aperture 431 may define a substantially constant cross-section, perpendicular to the longitudinal length of the flow director 408, at each location along the length of the flow director. Further, the base 402 may define a base opening 433 that may match a size and shape of the longitudinal aperture 431 extending through the flow director 408. Additionally, the flow director 408 may extend through the mouthpiece 416 (see, e.g., FIG. 8) or mate with an aperture in the mouthpiece having the same size and shape of the longitudinal aperture 431 extending the flow director. Accordingly, a smooth flow path may be defined through the cartridge 400 so as to allow flow therethrough with reduced pressure drop.

As noted above, the reservoir 412 may define an open space configured to receive an aerosol precursor composition. The reservoir 412 may be sealed such that aerosol precursor composition cannot escape therefrom other than through the atomizer 410 in the manner described herein. In this regard, the atomizer 410, and more particularly, the first and second connectors 428A, 428B, may engage the apertures 429A, 429B defined through the flow director 408 and through which the atomizer extends. For example, the first and second connectors 428A, 428B may respectively engage one of the apertures 429A, 429B via press fit. Thereby, the atomizer 410 may be sealed with respect to the flow director 408.

Further, the outer body 414 may be sealed to the mouthpiece 416 and a first end of the flow director 408 may be sealed to the mouthpiece. For example, the mouthpiece 416 may be ultrasonically welded to the outer body 414 and the flow director 408. Additionally, the outer body 414 may be sealed to the base 402. For example, in some embodiments the outer body 414 may be ultrasonically welded to the base 402.

However, in other embodiments it may be desirable to provide alternative mechanisms for sealing the reservoir 412. For example, it may be desirable to configure the cartridge 400 such that the atomizer 410 is removable. However, the atomizer 410 may be irremovably engaged with the flow director 408. Further, the flow director 408 may be irremovably engaged with the base 402 (e.g., ultrasonically welded, adhesively attached, or otherwise substantially permanently connected thereto). As such, replacement of the atomizer 410 may involve replacement of an assembly including the atomizer, the flow director 408, the first and second heating terminals 420, 421, the electronic component 406 (which may be received in a compartment defined between the base and the flow director), the electronic component terminal 404, and the base 402.

Accordingly, these components may be configured to be removable from a remainder of the cartridge 400. For example, as illustrated in FIG. 7, the base 402 may include a plurality of threads 402A configured to engage a plurality of threads 414A of the outer body 414 such that the outer body engages the base via threaded engagement. Although the threads 402A, 414A may form a seal, in some embodiments the cartridge 400 may further comprise a sealing member configured to seal the outer body 414 to the base 402. For example, an O-ring 432, which may comprise silicone or other resilient material, may extend around the base 402 and may be compressed between the outer body 414 and the base as the base is threaded into engagement with the outer body.

Further, the flow director 408 may releasably engage the mouthpiece 416. For example, as illustrated in FIG. 8, the flow director 408 may include a plurality of threads 418 configured to engage a plurality of threads 416A of the mouthpiece 416 such that the flow director engages the mouthpiece via threaded engagement. Although the threads 418, 416A may form a seal, in some embodiments the cartridge 400 may further comprise a sealing member configured to seal the flow director 408 to the mouthpiece 416. For example, an O-ring 434, which may comprise silicone or other resilient material, may extend around the flow director 408 and may be compressed between the flow director and the mouthpiece as the flow director is threaded into engagement with the mouthpiece.

As may be understood, the flow director 408 may threadingly engage the mouthpiece 416 (see, FIG. 8) simultaneously with the base 402 threadingly engaging the outer body 414 (see, FIG. 7). Further, a pitch of the threads 418 of the flow director 408 and the threads 416A of the mouthpiece 416 may be equal to a pitch of the threads 402A of the base 402 and the threads 414A of the outer body 414 to allow simultaneous engagement of the flow director and the mouthpiece and the base and the outer body without one set of threads binding before the other, thereby allowing the threads to form a seal by themselves and/or compressing the O-rings 432, 434 to form a seal.

Accordingly, by employing the threads 402A, 418, 414A, 416A, the cartridge 400 may be configured such that an assembly including the atomizer 410 may be removed and replaced. In this regard, the assembly including the atomizer 410 may be replaced when the useful life of the atomizer is complete, or the assembly may be replaced with a differing assembly including a differing atomizer that may, for example, be configured to produce a greater or lesser amount of aerosol with each puff.

As noted above, in some embodiments an assembly including the atomizer 410 may be replaceable such that a new atomizer may be provided when the atomizer reaches the end of its useable life. In this regard, in some embodiments the cartridge 400 may be refillable such that the cartridge 400 may be repeatedly reused.

Thus, the cartridge 400 may include features configured to facilitate refilling. For example, as illustrated in FIG. 7, the base 402 may define one or more fill ports 436. Thus, the open space defined by the reservoir 412 within the outer housing 414 may receive aerosol precursor composition directed through the one or more fill ports 436. Further, the one or more fill ports 436 may respectively comprise a one-way valve 438. The one-way valves 438 may be configured to allow flow of the aerosol precursor composition through the fill ports 436 into the reservoir 412, and prevent flow outwardly therefrom. For example, the one-way valves 438 may comprise diaphragm check valves, which may be formed from silicone or other resilient material and which may be biased to a closed configuration. Accordingly, a nozzle or extension of a refilling bottle may engage the filling port(s) 436 and/or the one way valve(s) 438 and direct aerosol precursor composition therethrough to refill the cartridge 400. In some embodiments the outer body 414 may be transparent or translucent along at least a portion thereof, such that a user may view the quantity of aerosol precursor composition contained therein, which may be useful to determine the level of aerosol precursor composition in the reservoir 412 during use and refilling of the cartridge 400.

Example embodiments of one-way valves that may be included in the cartridge 400 and associated refilling bottles and other aerosol precursor composition refilling components are described in U.S. patent application Ser. No. 15/165,928 to Sebastian et al., filed May 26, 2016 and U.S. Pat. Appl. Pub. No. 2016/0217882 to Davis et al., which are incorporated herein by reference in their entireties. Further, U.S. Pat. Appl. Pub. No. 2017/0013880 to O'Brien et al., discloses an aerosol delivery device including a refillable reservoir and a container for refilling the reservoir, and is incorporated herein by reference in its entirety.

In some embodiments the refilling bottle may threadingly engage the cartridge, snap into engagement therewith, or otherwise create a secure connection with the cartridge. The refilling bottle may then dispense the aerosol precursor composition into the cartridge by pumping or squeezing the refilling bottle, or by allowing pressurized fluid within the refilling bottle to expel the aerosol precursor composition into the cartridge. In some embodiments the filling port(s) may be configured to receive aerosol precursor composition from a refilling bottle that is also configured to refill a so-called "tank," which defines a relatively large reservoir for an aerosol delivery device. For example, the filling ports may be sized and configured to receive the nozzle of a tank refilling bottle, or the tank refilling bottle may be provided with a second nozzle configured to engage the filling port of the cartridge. Accordingly, the reservoir of the cartridge may be refilled with embodiments of refilling bottles that may be employed to refill multiple types of aerosol delivery devices.

Thus, the cartridge of the present disclosure may be refilled and reused. As may be understood, reuse of the cartridge may provide cost savings and reduce the amount of waste associated with use of the cartridge as compared to single-use disposable cartridges. As noted above, cartridges for aerosol delivery devices have traditionally employed fibrous wicks to transport aerosol precursor composition to a heating element. In view of the relatively short lifespan of suck wicks, cartridges have not generally been configured to be refillable. However, by employing a porous monolith as the liquid transport element, and/or by configuring the atomizer such that it is replaceable, and/or utilizing the liquid transport element itself as the heater, as described herein, the cartridge may be refilled and reused repeatedly.

In an additional embodiment an aerosol delivery device operation method is provided. As illustrated in FIG. 9, the method may include retaining an aerosol precursor composition in a reservoir defined between a flow director and an outer body, the flow director extending between a first flow director end and a second flow director end at operation 502. Further, the method may include directing the aerosol precursor composition from the reservoir through a liquid transport element of an atomizer extending through the flow director at a position between the first flow director end and the second flow director end at operation 504. The method may additionally include receiving an electrical current through a heating element of the atomizer at operation 506. The method may further include vaporizing at least a portion of the aerosol precursor composition to produce an aerosol within the flow director at operation 508.

In some embodiments the method may further include receiving the aerosol precursor composition through one or more fill ports defined in a base. Directing the aerosol precursor composition through the liquid transport element at operation 504 may include directing the aerosol precursor composition through a capillary channel. Directing the aerosol precursor composition through the liquid transport element at operation 504 may further include directing the aerosol precursor composition through a porous monolith to the heating element.

In some embodiments receiving the electrical current through the heating element at operation 506 may include receiving the electrical current through a wire defining a plurality of coils extending around the liquid transport element. The method may further include directing the aerosol out of the flow director through a mouthpiece. Additionally, the method may include retaining the aerosol precursor composition in the reservoir with a seal between the outer body and the base. Further, the method may include retaining the aerosol precursor composition in the reservoir with a seal between the mouthpiece and the outer body and a seal between the mouthpiece and the flow director.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
   an outer body;
   a base;
   a flow director extending from a first flow director end to a second flow director end through the outer body such that a reservoir is defined between the flow director and the outer body, the reservoir defining an open space configured to receive an aerosol precursor composition; and
   an atomizer extending through the flow director at a position between the first flow director end and the second flow director end, the atomizer including a liquid transport element and a heating element configured to vaporize at least a portion of the aerosol precursor composition to produce an aerosol within the flow director.

2. The aerosol delivery device of claim 1, wherein the liquid transport element comprises a capillary channel extending therethrough.

3. The aerosol delivery device of claim 2, wherein the liquid transport element comprises a porous monolith.

4. The aerosol delivery device of claim 3, wherein the heating element comprises a wire defining a plurality of coils extending around the liquid transport element.

5. The aerosol delivery device of claim 4, further comprising first and second connectors contacting the coils at first and second opposing ends of the heating element.

6. The aerosol delivery device of claim 1, wherein a longitudinal axis of the liquid transport element extends substantially perpendicularly to a longitudinal axis of the flow director.

7. The aerosol delivery device of claim 1, wherein the outer body is sealed to the base.

8. The aerosol delivery device of claim 7, wherein the outer body engages the base via threaded engagement.

9. The aerosol delivery device of claim 8, further comprising an O-ring is compressed between the outer body and the base.

10. The aerosol delivery device of claim 1, further comprising a mouthpiece, wherein the mouthpiece is sealed to the outer body and the flow director.

11. The aerosol delivery device of claim 1, wherein the base comprises one or more fill ports configured to receive the aerosol precursor composition therethrough.

12. The aerosol delivery device of claim 1, wherein the atomizer is sealed to the flow director.

13. An aerosol delivery device operation method, comprising:
    retaining an aerosol precursor composition in a reservoir defined between a flow director and an outer body, the flow director extending between a first flow director end and a second flow director end;
    directing the aerosol precursor composition from the reservoir through a liquid transport element of an atomizer extending through the flow director at a position between the first flow director end and the second flow director end;
    receiving an electrical current through a heating element of the atomizer; and
    vaporizing at least a portion of the aerosol precursor composition to produce an aerosol within the flow director.

14. The aerosol delivery device operation method of claim 13, further comprising receiving the aerosol precursor composition through one or more fill ports defined in a base.

15. The aerosol delivery device operation method of claim 13, wherein directing the aerosol precursor composition through the liquid transport element comprises directing the aerosol precursor composition through a capillary channel.

16. The aerosol delivery device operation method of claim 15, wherein directing the aerosol precursor composition through the liquid transport element further comprises directing the aerosol precursor composition through a porous monolith to the heating element.

17. The aerosol delivery device operation method of claim 13, wherein receiving the electrical current through the heating element comprises receiving the electrical current through a wire defining a plurality of coils extending around the liquid transport element.

18. The aerosol delivery device operation method of claim 13, further comprising directing the aerosol out of the flow director through a mouthpiece.

19. The aerosol delivery device operation method of claim 13, further comprising retaining the aerosol precursor composition in the reservoir with a seal between the outer body and the base.

20. The aerosol delivery device operation method of claim 13, further comprising retaining the aerosol precursor composition in the reservoir with a seal between the mouthpiece and the outer body and a seal between the mouthpiece and the flow director.

* * * * *